United States Patent
Mellican et al.

(10) Patent No.: US 7,745,622 B2
(45) Date of Patent: Jun. 29, 2010

(54) CRYSTALLINE N-(4-(4-AMMONIUMTHIENO[2,3-D]PYRIMIDIN-5-YL)PHENYL)-N'-(2-FLUORO-5-(TRIFLUOROMETHYL)PHENYL) UREA BENZENESULFONATE

(75) Inventors: Sean M. Mellican, Gurnee, IL (US); Cathie L. Linton, Waukegan, IL (US); Jianzhang Mei, Lake Forest, IL (US); Jason S. Tedrow, Santa Monica, CA (US); Nahathai Charukamnoetkanok, Pittsburgh, PA (US); Rodger Henry, Wildwood, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 654 days.

(21) Appl. No.: 11/642,408

(22) Filed: Dec. 20, 2006

(65) Prior Publication Data

US 2007/0161659 A1 Jul. 12, 2007

Related U.S. Application Data

(60) Provisional application No. 60/754,415, filed on Dec. 28, 2005.

(51) Int. Cl.
| | |
|---|---|
| C07D 495/04 | (2006.01) |
| A61K 31/519 | (2006.01) |
| A61P 35/04 | (2006.01) |
| A61P 35/02 | (2006.01) |
| A61P 17/06 | (2006.01) |
| A61P 9/12 | (2006.01) |

(52) U.S. Cl. .................... 544/278; 514/260.1
(58) Field of Classification Search ................. 544/278; 514/260.1

See application file for complete search history.

(56) References Cited

U.S. PATENT DOCUMENTS

| 7,427,623 B2 | 9/2008 | Adams et al. | |
|---|---|---|---|
| 2005/0004142 A1 * | 1/2005 | Adams et al. | ............ 514/260.1 |

OTHER PUBLICATIONS

Berge (Journal of Pharmaceutical Sciences, 1977, 66(1), pp. 1-19).*
U.S. Appl. No. 11/642,397, filed Dec. 20, 2006, Sean M. Mellican.
U.S. Appl. No. 11/642,497, filed Dec. 20, 2006, Sean M. Mellican.
U.S. Appl. No. 11/642,491, filed Dec. 20, 2006, Sean M. Mellican.
U.S. Appl. No. 11/642,201, filed Dec. 20, 2006, Sean M. Mellican.
U.S. Appl. No. 11/642,399, filed Dec. 20, 2006, Sean M. Mellican.
U.S. Appl. No. 11/642,396, filed Dec. 20, 2006, Sean M. Mellican.

* cited by examiner

*Primary Examiner*—Susanna Moore
(74) *Attorney, Agent, or Firm*—Glen J. Gesicki

(57) ABSTRACT

A crystalline N-(4-(4-aminothieno[2,3-d]pyrimidin-5-yl)phenyl)-N'-(2-fluoro-5-(trifluoromethyl)phenyl)urea benzenesulfonate characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.724°±0.002° and 84.067±0.002, respectively, ways to make it, compositions comprising it, and methods of treatment using it are disclosed.

2 Claims, No Drawings

US 7,745,622 B2

CRYSTALLINE N-(4-(4-AMMONIUMTHIENO [2,3-D]PYRIMIDIN-5-YL)PHENYL)-N'-(2-FLUORO-5-(TRIFLUOROMETHYL)PHENYL) UREA BENZENESULFONATE

This application claims priority to U.S. Provisional Application Ser. No. 60/754,415, Dec. 28, 2005.

FIELD OF THE INVENTION

This invention pertains to a crystalline N-(4-(4-ammoniumthieno[2,3-d]pyrimidin-5-yl)phenyl)-N'-(2-fluoro-5-(trifluoromethyl)phenyl)urea benzenesulfonate, ways to make it, compositions comprising it and methods of treatment using it.

BACKGROUND OF THE INVENTION

The compound N-(4-(4-aminothieno[2,3-d]pyrimidin-5-yl)phenyl)-N'-(2-fluoro-5-(trifluoromethyl)phenyl)urea is useful for treating diseases caused or exascerbated by upregulation or overexpression of protein tyrosine kinases.

Because the crystallinity of salts of compounds may effect, among other physical and mechanical properties, their solubility, dissolution rate, hardness, compressability and melting point, there is an existing need in the process and therapeutic arts for identification of crystalline salts of N-(4-(4-aminothieno[2,3-d]pyrimidin-5-yl)phenyl)-N'-(2-fluoro-5-(trifluoromethyl)phenyl)urea and ways to reproducibly make them.

SUMMARY OF THE INVENTION

One embodiment of this invention, therefore, pertains to crystalline N-(4-(4-ammoniumthieno[2,3-d]pyrimidin-5-yl)phenyl)-N'-(2-fluoro-5-(trifluoromethyl)phenyl)urea benzenesulfonate characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.724°±0.002° and 84.067±0.002, respectively.

Another embodiment pertains to crystalline N-(4-(4-ammoniumthieno[2,3-d]pyrimidin-5-yl)phenyl)-N'-(2-fluoro-5-(trifluoromethyl)phenyl)urea benzenesulfonate having substantial crystalline purity and characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.724°±0.002° and 84.067±0.002, respectively.

Still another embodiment pertains to a composition comprising an excipient and crystalline N-(4-(4-ammoniumthieno[2,3-d]pyrimidin-5-yl)phenyl)-N'-(2-fluoro-5-(trifluoromethyl)phenyl)urea benzenesulfonate characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.7240±0.002° and 84.067±0.002, respectively.

Still another embodiment pertains to a method or treating a patient having a disease caused or exascerbated by upregulation or overexpression of protein tyrosine kinases comprising administering thereto a therapeutically effective amount of crystalline N-(4-(4-ammoniumthieno[2,3-d]pyrimidin-5-yl)phenyl)-N'-(2-fluoro-5-(trifluoromethyl)phenyl)urea benzenesulfonate characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.7240±0.002° and 84.067±0.002, respectively.

Still another embodiment pertains to a process for making a crystalline N-(4-(4-ammoniumthieno[2,3-d]pyrimidin-5-yl)phenyl)-N'-(2-fluoro-5-(trifluoromethyl)phenyl)urea benzenesulfonate, said process comprising:

providing a mixture comprising N-(4-(4-aminothieno[2,3-d]pyrimidin-5-yl)phenyl)-N'-(2-fluoro-5-(trifluoromethyl)phenyl)urea, benzenesulfonic acid and solvent wherein said N-(4-(4-aminothieno[2,3-d]pyrimidin-5-yl)phenyl)-N'-(2-fluoro-5-(trifluoromethyl)phenyl)urea and said benzenesulfonic acid are completely dissolved in said solvent;

causing crystalline N-(4-(4-ammoniumthieno[2,3-d]pyrimidin-5-yl)phenyl)-N'-(2-fluoro-5-(trifluoromethyl)phenyl)urea benzenesulfonate to exist in said mixture, said crystalline N-(4-(4-ammoniumthieno[2,3-d]pyrimidin-5-yl)phenyl)-N'-(2-fluoro-5-(trifluoromethyl)phenyl)urea benzenesulfonate, when isolated, characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.724°±0.002° and 84.067±0.002, respectively; and isolating said N-(4-(4-ammoniumthieno[2,3-d]pyrimidin-5-yl)phenyl)-N'-(2-fluoro-5-(trifluoromethyl)phenyl)urea benzenesulfonate.

Still another embodiment pertains to a process for making a crystalline N-(4-(4-ammoniumthieno[2,3-d]pyrimidin-5-yl)phenyl)-N'-(2-fluoro-5-(trifluoromethyl)phenyl)urea benzenesulfonate, said process comprising:

providing a mixture comprising N-(4-(4-aminothieno[2,3-d]pyrimidin-5-yl)phenyl)-N'-(2-fluoro-5-(trifluoromethyl)phenyl)urea and ethanol, incorporating benzenesulfonic acid into said mixture and heating said mixture at a temperature between about 40° C. and 100° C.;

cooling said mixture to a temperature between about 0° C. and 25° C.; and isolating said N-(4-(4-ammoniumthieno[2,3-d]pyrimidin-5-yl)phenyl)-N'-(2-fluoro-5-(trifluoromethyl)phenyl)urea benzenesulfonate.

Still another embodiment pertains to N-(4-(4-ammoniumthieno[2,3-d]pyrimidin-5-yl)phenyl)-N'-(2-fluoro-5-(trifluoromethyl)phenyl)urea benzenesulfonate prepared by the foregoing processes.

DETAILED DESCRIPTION OF THE INVENTION

This invention pertains to discovery of a crystalline N-(4-(4-ammoniumthieno[2,3-d]pyrimidin-5-yl)phenyl)-N'-(2-fluoro-5-(trifluoromethyl)phenyl)urea benzenesulfonate, ways to characterize it, compositions containing it and methods of treating diseases caused or exascerbated by upregulation or overexpression of protein tyrosine kinases using it.

The term "diseases caused or exascerbated by upregulation or overexpression of protein tyrosine kinases," as used herein, means angiogenic diseases (e.g. diabetic retinopathy, retinopathy of prematurity, choroidal neovascularization due to age-related macular degeneration, infantile hemangiomas, cancer (lung, breast, stomach, bladder, colon, pancreatic, ovarian, prostate and rectal cancer and hematopoietic malignancies (leukemia and lymphoma), glioblastoma, infantile hemangioma)) (Lab. Investig. (1992), 67(4), 519-528; Anat. Rec. (1997), 249(1), 63-73; Int. J. Cancer (1995), 63(5), 694-701; Vasc. Biol. (1995), 15(11), 1857-6)), pulmonary hypertension in patients with thromboembolic disease (J.

Thorac. Cardiovasc. Surg. 2001, 122 (1), 65-73), and autoimmune diseases (psoriasis, kidney rejection, graft versus host disease).

The term "amorphous," as used herein, means a supercooled liquid substance or a viscous liquid which may appear as a solid but does not have a regularly repeating arrangement of molecules maintained over a long range. Amorphous substances do not have a melting point but soften or flow above a certain temperature known as the glass transition temperature.

The term "crystalline," as used herein, means having a regularly repeating arrangement of molecules which is maintained over a long range or external face planes.

The term "N-(4-(4-ammoniumthieno[2,3-d]pyrimidin-5-yl)phenyl)-N'-(2-fluoro-5-(trifluoromethyl)phenyl)urea benzenesulfonate," as used herein, means The term "N-(4-(4-ammoniumthieno[2,3-d]pyrimidin-5-yl)phenyl)-N'-(2-fluoro-5-(trifluoromethyl)phenyl)urea benzenesulfonate," as used herein, means an amorphous form of N-(4-(4-ammoniumothieno[2,3-d]pyrimidin-5-yl)phenyl)-N'-(2-fluoro-5-(trifluoromethyl)phenyl)urea benzenesulfonate, a microcrystalline form of N-(4-(4-ammoniumthieno[2,3-d]pyrimidin-5-yl)phenyl)-N'-(2-fluoro-5-(trifluoromethyl)phenyl)urea benzenesulfonate, N-(4-(4-ammoniumthieno[2,3-d]pyrimidin-5-yl)phenyl)-N'-(2-fluoro-5-(trifluoromethyl)phenyl)urea benzenesulfonate in solution, a particular crystalline form of N-(4-(4-ammoniumthieno[2,3-d]pyrimidin-5-yl)phenyl)-N'-(2-fluoro-5-(trifluoromethyl)phenyl)urea benzenesulfonate or a mixture thereof.

The term "crystalline N-(4-(4-ammoniumthieno[2,3-d]pyrimidin-5-yl)phenyl)-N'-(2-fluoro-5-(trifluoromethyl)phenyl)urea benzenesulfonate," as used herein, means a particular crystalline form of N-(4-(4-ammoniumthieno[2,3-d]pyrimidin-5-yl)phenyl)-N'-(2-fluoro-5-(trifluoromethyl)phenyl)urea benzenesulfonate, including the crystalline N-(4-(4-ammoniumthieno[2,3-d]pyrimidin-5-yl)phenyl)-N'-(2-fluoro-5-(trifluoromethyl)phenyl)urea benzenesulfonate of this invention.

The term "crystalline N-(4-(4-ammoniumthieno[2,3-d]pyrimidin-5-yl)phenyl)-N'-(2-fluoro-5-(trifluoromethyl)phenyl)urea benzenesulfonate of this invention," as used herein, means crystalline N-(4-(4-ammoniumthieno[2,3-d]pyrimidin-5-yl)phenyl)-N'-(2-fluoro-5-(trifluoromethyl)phenyl) urea benzenesulfonate characterized, in the triclinic crystal system and P-1 space group when measured with radiation at 0.7107 Å, by lattice parameters a, b and c of 7.800 Å±0.001 Å, 13.406 Å±0.002 Å and 13.554 Å±0.002 Å, respectively and $\alpha$, $\beta$ and $\gamma$ of 67.155°±0.002°, 79.724°±0.002° and 84.067°±0.002°, respectively.

Unless stated otherwise, percentages herein are weight/weight (w/w) percentages.

The term "substantial crystalline purity," as used herein, means at least about 95% crystalline purity, preferably about 97% crystalline purity, more preferably about 99% crystalline purity, and most preferably about 100% crystalline purity.

The term "crystalline purity," as used herein, means percentage of a particular crystalline form of a compound in a sample which may contain amorphous form of the compound, one or more than one other crystalline forms of the compound other than the crystalline form of the compound of this invention, or a mixture thereof.

The term "substantial chemical purity," as used herein, means about 95% chemical purity, preferably about 97% chemical purity, more preferably about 98% chemical purity, and most preferably about 100% chemical purity.

This invention is also meant to include mixtures comprising crystalline N-(4-(4-ammoniumthieno[2,3-d]pyrimidin-5-yl)phenyl)-N'-(2-fluoro-5-(trifluoromethyl)phenyl)urea benzenesulfonate of this invention in combination with one or more than one other crystalline forms of N-(4-(4-ammoniumthieno[2,3-d]pyrimidin-5-yl)phenyl)-N'-(2-fluoro-5-(trifluoromethyl)phenyl)urea benzenesulfonate.

It is meant to be understood that each component of mixtures consisting essentially of two or more forms of N-(4-(4-ammoniumthieno[2,3-d]pyrimidin-5-yl)phenyl)-N'-(2-fluoro-5-(trifluoromethyl)phenyl)urea benzenesulfonate may have varying degrees of chemical purity and that, in a preferred embodiment for the practice of this invention, in mixtures comprising different forms of N-(4-(4-ammoniumthieno[2,3-d]pyrimidin-5-yl)phenyl)-N'-(2-fluoro-5-(trifluoromethyl)phenyl)urea benzenesulfonate, each component is substantially chemically pure.

The term "solvent," as used herein, means a liquid substance in which a compound is soluble or partially soluble enough at a given concentration to dissolve or partially dissolve the compound.

The term "anti-solvent," as used herein, means a liquid in which a compound is insoluble enough at a given concentration to be effective for precipitating that compound.

Solvents and anti-solvents may be mixed with or without emulsification.

It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

Causing a crystalline N-(4-(4-ammoniumthieno[2,3-d]pyrimidin-5-yl)phenyl)-N'-(2-fluoro-5-(trifluoromethyl)phenyl)urea benzenesulfonate to exist in a mixture in which it has completely dissolved is known as nucleation.

For the practice of this invention, nucleation may be made to occur by means such as solvent removal, temperature change, solvent-miscible anti-solvent addition, solvent-immiscible anti-solvent addition, seed crystal addition of a crystalline N-(4-(4-ammoniumthieno[2,3-d]pyrimidin-5-yl)phenyl)-N'-(2-fluoro-5-(trifluoromethyl)phenyl)urea benzenesulfonate, chafing or scratching the interior of the container, preferably a glass container, in which nucleation is meant to occur with an implement such as a glass rod or a glass bead or beads, or a combination of the foregoing.

For the practice of this invention, nucleation may be followed by crystal growth, accompanied by crystal growth, or followed and accompanied by crystal growth during which, and as a result of which, the percentage of a crystalline N-(4-(4-ammoniumthieno[2,3-d]pyrimidin-5-yl)phenyl)-N'-(2-fluoro-5-(trifluoromethyl)phenyl)urea benzenesulfonate increases.

It is meant to be understood that airborne seed crystals of a crystalline N-(4-(4-ammoniumthieno[2,3-d]pyrimidin-5-yl)phenyl)-N'-(2-fluoro-5-(trifluoromethyl)phenyl)urea benzenesulfonate may also cause nucleation in a mixture comprising N-(4-(4-ammoniumthieno[2,3-d]pyrimidin-5-yl)phenyl)-N'-(2-fluoro-5-(trifluoromethyl)phenyl)urea benzenesulfonate and solvent wherein the N-(4-(4-ammoniumthieno[2,3-d]pyrimidin-5-yl)phenyl)-N'-(2-fluoro-5-(trifluoromethyl)phenyl)urea benzenesulfonate has completely dissolved.

The term "seed crystal," as used herein, means a particular crystalline form of a substance having mass. It is meant to be understood that such a crystal may be small enough to be airborne or invisible to the eye without means of detection.

The term "isolating" as used herein, means separating a crystalline N-(4-(4-ammoniumthieno[2,3-d]pyrimidin-5-yl)phenyl)-N'-(2-fluoro-5-(trifluoromethyl)phenyl)urea benzenesulfonate and solvent, anti-solvent, or a mixture comprising solvent and anti-solvent. This is typically accomplished by means such as centrifugation, filtration with or without vacuum, filtration with positive pressure, distillation, evaporation or a combination thereof.

A therapeutically acceptable amount of a crystalline N-(4-(4-ammoniumthieno[2,3-d]pyrimidin-5-yl)phenyl)-N'-(2-fluoro-5-(trifluoromethyl)phenyl)urea benzenesulfonate depends on recipient of treatment, disorder being treated and severity thereof, composition containing it, time of administration, route of administration, duration of treatment, its potency, its rate of clearance and whether or not another drug is co-administered. The amount of a crystalline N-(4-(4-ammoniumthieno[2,3-d]pyrimidin-5-yl)phenyl)-N'-(2-fluoro-5-(trifluoromethyl)phenyl)urea benzenesulfonate used to make a composition to be administered daily to a patient in a single dose or in divided doses is from about 0.03 to about 200 mg/kg body weight. Single dose compositions contain these amounts or a combination of submultiples thereof.

A crystalline N-(4-(4-ammoniumthieno[2,3-d]pyrimidin-5-yl)phenyl)-N'-(2-fluoro-5-(trifluoromethyl)phenyl)urea benzenesulfonate may be administered with or without an excipient. Excipients include but are not limited to, for example, encapsulating materials and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising and made with a crystalline N-(4-(4-ammoniumthieno[2,3-d]pyrimidin-5-yl)phenyl)-N'-(2-fluoro-5-(trifluoromethyl)phenyl)urea benzenesulfonate to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising and made with a crystalline N-(4-(4-ammoniumthieno[2,3-d]pyrimidin-5-yl)phenyl)-N'-(2-fluoro-5-(trifluoromethyl)phenyl)urea benzenesulfonate to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising and made with a crystalline N-(4-(4-ammoniumthieno[2,3-d]pyrimidin-5-yl)phenyl)-N'-(2-fluoro-5-(trifluoromethyl)phenyl)urea benzenesulfonate to be administered osmotically include, for example, chlorofluorohydrocarbons, ethanol, water, mixtures thereof and the like. Excipients for preparation of compositions comprising and made with a crystalline N-(4-(4-ammoniumthieno[2,3-d]pyrimidin-5-yl)phenyl)-N'-(2-fluoro-5-(trifluoromethyl)phenyl)urea benzenesulfonate to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising and made with a crystalline N-(4-(4-ammoniumthieno[2,3-d]pyrimidin-5-yl)phenyl)-N'-(2-fluoro-5-(trifluoromethyl)phenyl)urea benzenesulfonate to be administered rectally or vaginally include, but are not limited to, cocoa butter, polyethylene glycol, wax, mixtures thereof and the like.

The following examples are presented to provide what is believed to be the most useful and readily understood description of procedures and conceptual aspects of this invention.

EXAMPLE 1

A mixture of 1-(4-nitrophenyl)ethanone (15 g), malononitrile (6 g), ammonium acetate (7 g) and acetic acid (10 mL) in benzene (200 mL) at reflux was stirred for 18 hours with azeotropic removal of water, cooled, poured into water, and extracted with ethyl acetate. The combined extracts were washed with water and brine and dried ($MgSO_4$), filtered and concentrated. The concentrate was flash chromatographed on silica gel with 25% ethyl acetate/hexanes.

EXAMPLE 2

EXAMPLE 58A (4.14 g) in ethanol (200 mL) and THF (80 mL) at 25° C. was treated sequentially with sulfur (621 mg) and triethylamine (1.82 mg), stirred for 18 hours and filtered. The filtrant was absorbed onto silica and flash column chromatographed with 3:2 hexanes/ethyl acetate.

EXAMPLE 3

EXAMPLE 2 (1.23 g) in formamide (20 mL) between 150° C. and 160° C. was stirred for 19 hours, cooled, and filtered.

EXAMPLE 4

EXAMPLE 3 (500 mg) in THF (30 mL), water (15 mL), and ethanol (40 mL) at 50° C. was treated with iron powder (0.616 g), heated between 70° C. and 80° C. for two hours and filtered through diatomaceous earth (Celite®) while hot. The filtrant was washed with THF (10 mL) and ethanol and the combined filtrates were concentrated. The concentrate was partitioned between water and ethyl acetate and the aqueous phase was extracted three times with ethyl acetate. The combined extracts were washed with brine and dried ($MgSO_4$), filtered and concentrated.

EXAMPLE 5

EXAMPLE 4 (40 mg) in dichloromethane (3 mL) at 0° C. was treated with 1-fluoro-2-isocyanato-4-(trifluoromethyl)benzene (24 μL), stirred for 18 hours while gradually warming to 25° C. and filtered. The filtrant was dried under vacuum. $^1$H NMR (300 MHz, DMSO-$d_6$) δ 9.40 (s, 1H); 8.98 (d, 1H); 8.63 (dd, 2.1 Hz, 1H); 8.35 (s, 1H); 7.63 (d, 2H); 7.55-7.39 (m, 5H).

EXAMPLE 6

EXAMPLE 5 in ethanol (100 mL) at 70° C. was treated with benzenesulfonic acid (2.12 g), cooled and filtered.

Single crystal data were obtained using an XDS-2000/X-ray diffractometer equipped with a 2 kW normal focus X-ray tube and a Peltier cooled germanium solid-state detector (Scintag Inc., Sunnyvale, Calif.). The data were processed using DMSNT software (version 1.37). The X-ray source was a molybdenum filament (Mo—Kα at 0.7107 Å) operated at 45 kV and 40 mA.

The foregoing is meant to be illustrative of the invention and not intended to limit it to the disclosed embodiments. Variations and changes obvious to one skilled in the art are intended to be within the scope and nature of the invention as defined in the claims.

We claim:

1. Crystalline N-(4-(4-ammoniumthieno[2,3-d]pyrimidin-5-yl)phenyl)-N'-(2-fluoro-5-(trifluoromethyl)phenyl)urea benzenesulfonate characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.724°±0.002° and 84.067±0.002, respectively.

2. Crystalline N-(4-(4-ammoniumthieno[2,3-d]pyrimidin-5-yl)phenyl)-N'-(2-fluoro-5-(trifluoromethyl)phenyl)urea benzenesulfonate having substantial crystalline purity and characterized in the triclinic crystal system and P-1 space group, when measured with radiation at 0.7107 Å, by lattice parameters a, b and c of 7.800 Å±0.001 Å, 13.406 Å±0.002 Å and 13.554 Å±0.002 Å, respectively and α, β and γ of 67.155±0.002, 79.724°±0.002° and 84.067±0.002, respectively.

* * * * *

UNITED STATES PATENT AND TRADEMARK OFFICE
CERTIFICATE OF CORRECTION

| | | |
|---|---|---|
| PATENT NO. | : 7,745,622 B2 | Page 1 of 1 |
| APPLICATION NO. | : 11/642408 | |
| DATED | : June 29, 2010 | |
| INVENTOR(S) | : Sean M. Mellican et al. | |

It is certified that error appears in the above-identified patent and that said Letters Patent is hereby corrected as shown below:

Column 1, Line 59 – please revise "79.7240±0.002°" to read as --79.724°±0.002°--

Column 2, Line 3 – please revise "γ of 67.155±0.002, 79.7240±0.002°" to read as --γ of 67.155±0.002, 79.724°±0.002°--

Signed and Sealed this
Twenty-fifth Day of December, 2012

David J. Kappos
*Director of the United States Patent and Trademark Office*